US00PP23211P3

(12) United States Plant Patent
Zaiger et al.

(10) Patent No.: US PP23,211 P3
(45) Date of Patent: Nov. 27, 2012

(54) INTERSPECIFIC TREE NAMED 'SWEET PIXIE'

(50) Latin Name: **Interspecific *Prunus* species**
Varietal Denomination: Sweet Pixie

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 125 days.

(21) Appl. No.: 12/930,511

(22) Filed: Jan. 10, 2011

(65) Prior Publication Data

US 2012/0180170 P1 Jul. 12, 2012

(51) Int. Cl.
*A01H 5/00* (2006.01)

(52) U.S. Cl. ..... Plt./180

(58) Field of Classification Search ..... Plt./180, Plt./181, 184
See application file for complete search history.

*Primary Examiner* — June Hwu

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Heavy and regular bearer of fruit.
3. Fruit with excellent flavor and eating quality.
4. Fruit with good handling and shipping quality.
5. Fruit with an average Brix of 20° with a good balance between acid and sugar.
6. Fruit with the ability to remain firm on the tree 3 weeks past maturity (shipping ripe).

1 Drawing Sheet

Botanical classification: Interspecific *Prunus* species.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of cherries, interspecific and plum trees, which are known to us, and mentioned herein, 'Royal Lee' Cherry (U.S. Plant Pat. No. 12,417), 'Bing' Cherry (non-patented), 'Stella' Cherry (non-patented), 'Nadia' Interspecific (U.S. Plant Pat. No. 19,842), the proprietary cherry selections '5.5GK110' and '21ZA1058', the proprietary plum selection '85EG395' and the proprietary interspecific selection '162LM354'.

STATEMENT REGARDING FEDERALLY SPONSORED RESEARCH AND DEVELOPMENT

Not applicable.

ORIGIN OF THE VARIETY

The new and distinct interspecific tree was originated by us from crosses between the following species [(*Prunus salicina*×*Prunus avium*)×*Prunus avium*]. The present variety was selected from a first generation cross between the proprietary selected seedlings '162LM354' and '21ZA1058'. The seed parent (162LM354) was developed by us from a proprietary plum seedling selection '85EG395' crossed with a proprietary cherry seedling selection '5.5GK110'. We developed the proprietary pollen parent (21ZA1058) by crossing the following cherry selections; 'Bing' Cherry (non-patented), 'Stella' Cherry (non-patented) and 'Royal Lee' Cherry (U.S. Plant Pat. No. 12,417). We budded a large number of these seedlings, growing on their own root, from this cross to older 'Nemaguard' Rootstock (non-patented) trees to induce earlier fruit production for evaluation. Under close and careful observation the present seedling exhibited desirable fruit and tree characteristics and was selected in 2004 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual reproduction.

SUMMARY OF THE NEW VARIETY

The present new and distinct variety of interspecific tree which includes [(Plum×Cherry)×Cherry] in its parentage is of large size, vigorous, upright growth and a productive and regular bearer of small to medium size, yellow-red flesh, firm fruit with excellent flavor and eating quality. The fruit is further characterized by holding firm on the tree 3 weeks past maturity (shipping ripe) and having good storage and shipping quality. In comparison to its seed parent (162LM354) the fruit is approximately 30 days earlier in maturity with superior eating quality. In comparison to its pollen parent (21ZA1058) the phenotype of the new variety, its tree and fruit characteristics, resembles its seed parent (plum like instead of cherry like), its fruit is larger in size and is approximately 50 days later in maturity. In comparison to the interspecific variety 'Nadia' (U.S. Plant Pat. No. 19,842) the fruit of the new variety is approximately 8 days earlier in maturity, has speckled yellow-red skin compared with dark red to purple and has yellow-red flesh compared with dark red.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens grown near Modesto, Calif., with color in accordance with Munsell book of Color published in 1958.

Tree:

*Size*.—Large, pruned to 3 to 3.5 meters in height and width for economical harvesting of fruit. Varies with different cultural practices.

*Vigor*.—Vigorous, tree growth of approximately 1.5 to 2 meters the first growing season. Varies with cultural practices, soil type, fertility and climatic conditions.

*Form*.—Upright growth.

*Branching habit*.—Upright, crotch angle approximately 30°, increases with heavy crop load.

*Productivity*.—Productive, thinning and spacing of fruit desirable for market size fruit.

*Bearer*.—Regular, adequate fruit set 5 consecutive years. No alternate bearing observed.

*Fertility*.—Self-sterile, pollinator required.

*Density*.—Medium dense, usually pruned to vase shape to increase sunlight and air movement to center of tree to enhance fruit color and spur growth.

*Hardiness*.—Hardy in all stone fruit growing areas of California. Tree grown in USDA Hardiness Zone 9. Winter chilling requirement approximately 900 hours at or below 45° F.

Trunk:

*Size*.—Medium to large. Average circumference of 46.9 cm at 38.1 cm above ground level on a 7 year old tree.

*Stocky*.—Medium stocky.

*Texture*.—Medium shaggy, becomes rougher with age.

*Color*.—Varies from 10YR 4/2 to 2.5Y 5/2.

Branches:

*Size*.—Medium. Average circumference 16.9 cm at 1.2 meters above ground. Crotch angle approximately 30°, increases with heavy fruit crop.

*Surface texture*.—New growth relatively smooth. Mature growth medium rough, roughness increases with age.

*Lenticels*.—Size — medium. Average number 26 in a 25.8 sq cm area. Average length 2.5 mm. Average width 1.3 mm. Color varies from 5YR 5/8 to 5YR 4/8.

*Color*.—New growth varies from 10Y 6/6 to 10Y 6/8. Old growth varies from 10YR 3/2 to 7.5YR 3/4, varies with age of growth.

Leaves:

*Size*.—Medium to large. Average length 100.4 mm. Average width 40.8 mm.

*Form*.—Oblanceolate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation.

*Petiole*.—Average length 17.3 mm. Average width 1.5 mm. Longitudinally grooved. Very short pubescence. Color varies from 5GY 6/6 to 5R 3/6 where exposed to sun.

*Glands*.—Globose. Size — small. Average length 0.9 mm. Average diameter 0.4 mm. Average number — 2, varies from 1 to 3. Located primarily on the lower portion of leaf blade and upper portion of petiole. Color varies from 2.5GY 6/6 to 2.5GY 5/6.

*Stipules*.—Average number 2. Average length 4.2 mm. Margin — serrate. Color — 5GY 5/6.

*Color*.—Upper surface varies from 5GY 4/8 to 5GY 4/2. Lower surface varies from 5GY 5/4 to 7.5GY 4/4. Midvein color varies from 5GY 6/6 to 5GY 5/6.

Flower buds:

*Size*.—Small. Average length 7.0 mm. Average diameter 4.7 mm.

*Hardiness*.—Hardy with respect to California winters.

*Form*.—Conical, becoming elongated before opening.

*Pedicel*.—Average length 9.6 mm. Average width 0.5 mm. Color varies from 2.5GY 6/8 to 5GY 5/8. Surface — glabrous.

*Color*.—N 9.5/(white).

*Number of buds per spur*.—Average number 7, varies from 5 to 13. Varies with age of flower spur.

Flowers:

*Blooming period*.—Date of First Bloom Feb. 26, 2010. Date of Petal Fall Mar. 5, 2010, varies slightly with climatic conditions.

*Size*.—Small to medium. Average height 7.7 mm. Average diameter 17.6 mm.

*Petals*.—Relative position of petal margins — free. Normally 5, alternately arranged to the sepals. Size — small. Average length 8.8 mm. Average width 5.7 mm. Form varies from globose to slightly elliptical. Margin — sinuate. Both upper and lower surfaces glabrous. Color — N 9.5/(white).

*Sepals*.—Normally 5, alternately arranged to the petals. Size — small. Average length 2.7 mm. Average width 2.1 mm. Shape — triangular, apex rounded. Margin — entire. Both upper and lower surfaces glabrous. Color — upper surface varies from 2.5GY 6/8 to 5GY 6/6. Lower surface varies from 2.5GY 6/8 to 5GY 6/8.

*Stamens*.—Average number per flower 30, varies from 19 to 36. Average filament length 5.6 mm. Filament color N 9.5/(white). Anther color varies from 5Y 8.5/6 to 7.5Y 8/8.

*Pollen*.—Self-sterile, pollinator required. Color varies from 5Y 8/6 to 5Y 8/8.

*Pistil*.—Normally 1. Surface — glabrous. Average length 7.9 mm. Position of stigma approximately 1.8 mm above anthers. Color varies from 10Y 8/6 to 2.5GY 8/6.

*Fragrance*.—Heavy aroma.

*Color*.—N 9.5/(white).

*Number flowers per flower bud*.—Average 3, varies from 1 to 4. Pedicel — medium. Average length 11.3 mm. Average width 0.6 mm. Color varies from 2.5GY 5/8 to 5GY 5/8. Surface — glabrous.

Fruit:

*Maturity when described*.—Firm ripe.

*Date of first picking*.—Jun. 27, 2010.

*Date of last picking*.—Jul. 5, 2010, varies slightly with climatic conditions.

*Size*.—Small to medium. Average diameter axially 40.3 mm. Average transversely in suture plane 40.4 mm. Average weight 42.6 grams, varies slightly with fertility of the soil, amount of thinning and climatic conditions.

*Form*.—Globose.

*Suture*.—Very slightly lipped, extends from base to apex.

*Ventral surface*.—Smooth to slightly lipped.

*Apex*.—Nearly rounded.

*Base*.—Flat.

*Stem cavity*.—Rounded to slightly elongated in suture plane. Average depth 2.3 mm. Average diameter 2.0 mm.

Stem:

*Size*.—Medium. Average length 16.9 mm. Average diameter 1.4 mm.

*Color*.—Varies from 10Y 6/8 to 2.5GY 6/8.

Flesh:

*Ripens*.—Evenly.

*Texture*.—Firm, meaty.

*Fibers*.—Few, small and tender.

*Firmness*.—Good, comparable to commercial plum varieties.

*Aroma*.—Very slight.

*Amydgalin*.—Undetected.

*Eating quality*.—Excellent.

*Flavor*.—Excellent, a good balance between acid and sugar.

*Juice*.—Moderate amount, enhances flavor.

*Brix*.—Average 20.2°, varies slightly with amount of fruit per tree and climatic conditions.

*Color*.—Varies from 2.5Y 8/8 to 7.5R 4/10 next to the skin. Pit cavity varies from 2.5YR 4/6 to 2.5YR 4/8.

*Pit cavity*.—Shape — ovoid. Average length 23.2 mm. Average width 17.3 mm. Average depth 4.8 mm.

Skin:

*Thickness*.—Medium.

*Surface*.—Smooth.

*Bloom*.—Moderate amount.

*Tendency to crack*.—None.

*Color*.—Ground color varies from 10Y 7/4 to 2.5GY 8/6. Overspread with 5R 3/8 to 7.5R 3/8. Fruit with randomly spaced areas of ground color exposed to give a speckled pattern to skin surface areas.

*Tenacity*.—Tenacious to flesh.

*Astringency*.—Undetected.

Stone:

*Type*.—Clingstone.

*Size*.—Medium. Average length 21.1 mm. Average width 15.6 mm. Average thickness 8.6 mm.

*Form*.—Ovoid.

*Base*.—Flat.

*Apex*.—Rounded to slight tip. Average length 0.5 mm.

*Surface*.—Very small pits throughout. One shallow groove on each side of the suture, extending from base to apex.

*Sides*.—Unequal, one side extending further from the suture plane.

*Ridges*.—A small narrow ridge on each side of suture extending from base to apex.

*Tendency to split*.—None.

*Color*.—Varies from 7.5YR 5/6 to 7.5YR 5/8 when dry.

Kernel:

*Size*.—Medium. Average length 13.0 mm. Average width 9.0 mm. Average depth 5.3 mm.

*Shape*.—Ovate.

*Viability*.—Viable, complete embryo development.

*Skin*.—Color varies from 5YR 9/4 to 7.5Y 9/4.

Use:

*Dessert*.—Market — local and long distance.

Keeping quality: Good, held firm in cold storage for 3 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program The present new variety of interspecific tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

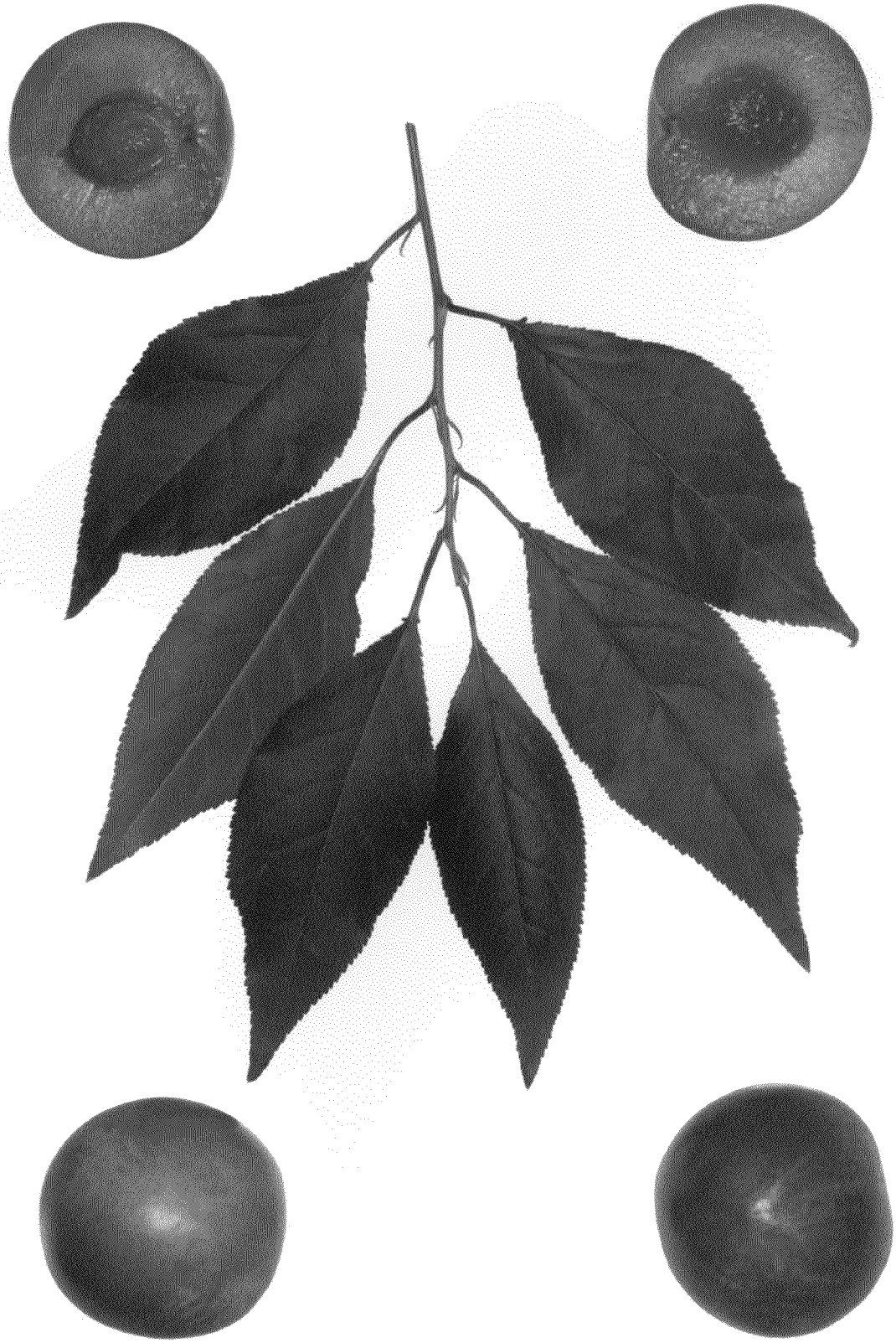

* * * * *